United States Patent
Jain et al.

(10) Patent No.: US 11,475,632 B1
(45) Date of Patent: Oct. 18, 2022

(54) SYSTEM AND METHOD FOR ELECTRO-ANATOMICAL MAPPING (EAM) BASED ON A SURFACE MESH

(71) Applicant: Neucures Inc., Los Angeles, CA (US)

(72) Inventors: Rohit Jain, Danville, CA (US); Kappagantula Gopalakrishna Murty, Nanaimo (CA); Vijay Raghavan Dharmapuri Murali, Bengaluru (IN); Robert L. Lux, Park City, UT (US)

(73) Assignee: NEUCURES INC, Los Angeles, CA (US)

( * ) Notice: Subject to any disclaimer, the term of this patent is extended or adjusted under 35 U.S.C. 154(b) by 0 days.

(21) Appl. No.: 17/125,509

(22) Filed: Dec. 17, 2020

(51) Int. Cl.
*G06T 17/20* (2006.01)
*G06T 19/20* (2011.01)
*A61B 5/367* (2021.01)

(52) U.S. Cl.
CPC ............ *G06T 17/205* (2013.01); *A61B 5/367* (2021.01); *G06T 19/20* (2013.01); *G06T 2210/41* (2013.01); *G06T 2210/56* (2013.01); *G06T 2219/2021* (2013.01)

(58) Field of Classification Search
CPC combination set(s) only.
See application file for complete search history.

(56) References Cited

U.S. PATENT DOCUMENTS

| | | | | |
|---|---|---|---|---|
| 2009/0167755 A1* | 7/2009 | Voth | ........................ | G06T 17/20 345/419 |
| 2013/0138404 A1* | 5/2013 | Carbonera | ............ | G06T 17/205 703/2 |
| 2018/0158238 A1* | 6/2018 | Cohen | ..................... | A61B 5/743 |
| 2019/0362548 A1* | 11/2019 | Hatanaka | ................ | G06T 17/20 |
| 2020/0202624 A1* | 6/2020 | Szasz | ...................... | G06T 17/20 |
| 2021/0236206 A1* | 8/2021 | Chopra | .................. | A61B 34/20 |

OTHER PUBLICATIONS

Tavard, François, et al. "Multimodal registration and data fusion for cardiac resynchronization therapy optimization." IEEE transactions on medical imaging 33.6 (2014): 1363-1372. (Year: 2014).*

* cited by examiner

*Primary Examiner* — Ryan M Gray
(74) *Attorney, Agent, or Firm* — HM Law Group LLP; Vani Moodley, Esq.

(57) ABSTRACT

Disclosed is a method for electro-anatomical mapping. In accordance with the method, surface mesh data is defined to represent the geometry of a myocardial surface. The mesh data comprises mesh points arranged to defined triangles on the myocardial surface and the mesh data is segmented into boundary areas. Point cloud data comprising a plurality of point cloud data points is received and each point cloud data point is assigned to a corresponding mesh point within a boundary area. The point cloud data point and its corresponding mesh point defines a mapping. For each mapping, a difference in a spatial location is determined between the points comprising the mapping. A warping function is selectively applied to spatially relocate the mesh point within each mapping based on the location of the corresponding point cloud data point within the mapping.

12 Claims, 4 Drawing Sheets

SYSTEM AND METHOD FOR ELECTRO-ANATOMICAL MAPPING (EAM) BASED ON A SURFACE MESH

CROSS-REFERENCE TO RELATED APPLICATIONS AND PRIORITY

The present application does not claim priority from any patent application.

TECHNICAL FIELD

Embodiments of the present invention relate to Electro-Anatomical Mapping (EAM) systems, more particularly EAM systems for surface reconstruction.

BACKGROUND

Electro-Anatomical mapping (EAM) systems can facilitate surface reconstruction, tagging of important anatomic landmarks and ablation lesions, display of diagnostic and mapping catheters without using fluoroscopy, activation mapping, and voltage (or scar) mapping.

EAM depends upon data collection for procedural success (activation mapping, substrate mapping, cardiac geometry).

EAM systems generate cardiac geometry using point cloud data comprising a set of points wherein each point is defined by its spatial position within a coordinate system. In order to generate the point cloud data, a catheter is moved within the intracardiac space while its position is tracked within the said space through magnetic sensing. Typically, the catheter has a magnetic tip whose spatial location can be tracked. The mapping process collects electrical recordings at a discrete at measurement sites where the catheter tip is in contact with the myocardial surface.

The electrical recordings from the measurement sites define a point cloud comprising a set of data points (X, Y and Z). To generate an electric anatomical map, the data points within the point cloud a use to construct a surface mesh that approximates anatomic structures.

SUMMARY

Before the present system and method for Electro-Anatomical Mapping (EAM) is described, it is to be understood that this application is not limited to the particular systems, and methodologies described, as there can be multiple possible embodiments which are not expressly illustrated in the present disclosure. It is also to be understood that the terminology used in the description is for the purpose of describing the particular versions or embodiments only and is not intended to limit the scope of the present application. This summary is provided to introduce concepts related to the system and method for generating point cloud data for electro-anatomical mapping. This summary is not intended to identify essential features of the claimed subject matter nor is it intended for use in determining or limiting the scope of the claimed subject matter.

In one implementation, a method for electro-anatomical mapping is disclosed. The method comprises defining surface mesh data to represent the geometry of a myocardial surface. The mesh data comprises mesh points arranged to defined triangles on the myocardial surface and the mesh data is segmented into boundary areas. The method further comprises receiving point cloud data comprising a plurality of point cloud data points and assigning each point cloud data point to a corresponding mesh point within a boundary area. The point cloud data point and its corresponding mesh point defines a mapping. The method further comprises for each mapping, determining a difference in a spatial location between the points comprising the mapping and selectively applying a warping function to spatially relocate the mesh point within each mapping based on the location of the corresponding point cloud data point within the mapping.

In another implementation, a system for electro-anatomical mapping is disclosed. The system comprises of a memory and a processor coupled to the memory. The processor is configured to execute instructions stored in the memory to define surface mesh data to represent the geometry of a myocardial surface. The mesh data comprises mesh points arranged to defined triangles on the myocardial surface, and the mesh data is segmented into boundary areas. The processor is configured to execute instructions stored in the memory to receive point cloud data comprising a plurality of point cloud data points; and assign each point cloud data point to a corresponding mesh point within a boundary area. The point cloud data point and its corresponding mesh point defines a mapping. The processor is further configured to execute instructions stored in the memory to determine a difference in a spatial location for each mapping between the points comprising the mapping and selectively apply a warping function to spatially relocate the mesh point within each mapping based on the location of the corresponding point cloud data point within the mapping.

DETAILED DESCRIPTION

Some embodiments of the present disclosure, illustrating all its features, will now be discussed in detail. The words "comprising", "receiving", "determining", "generating" and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a", "an" and "the" include plural references unless the context clearly dictates otherwise. Although any systems and methods similar or equivalent to those described herein can be used in the practice or testing of embodiments of the present disclosure, the exemplary system and method for generating point cloud data for electro-anatomical mapping are now described. The disclosed embodiments of the system and method for generating point cloud data for electro-anatomical mapping are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure for system and method for generating point cloud data for electro-anatomical mapping is not intended to be limited to the embodiments illustrated, but is to be accorded the widest scope consistent with the principles and features described herein.

Figure 1:
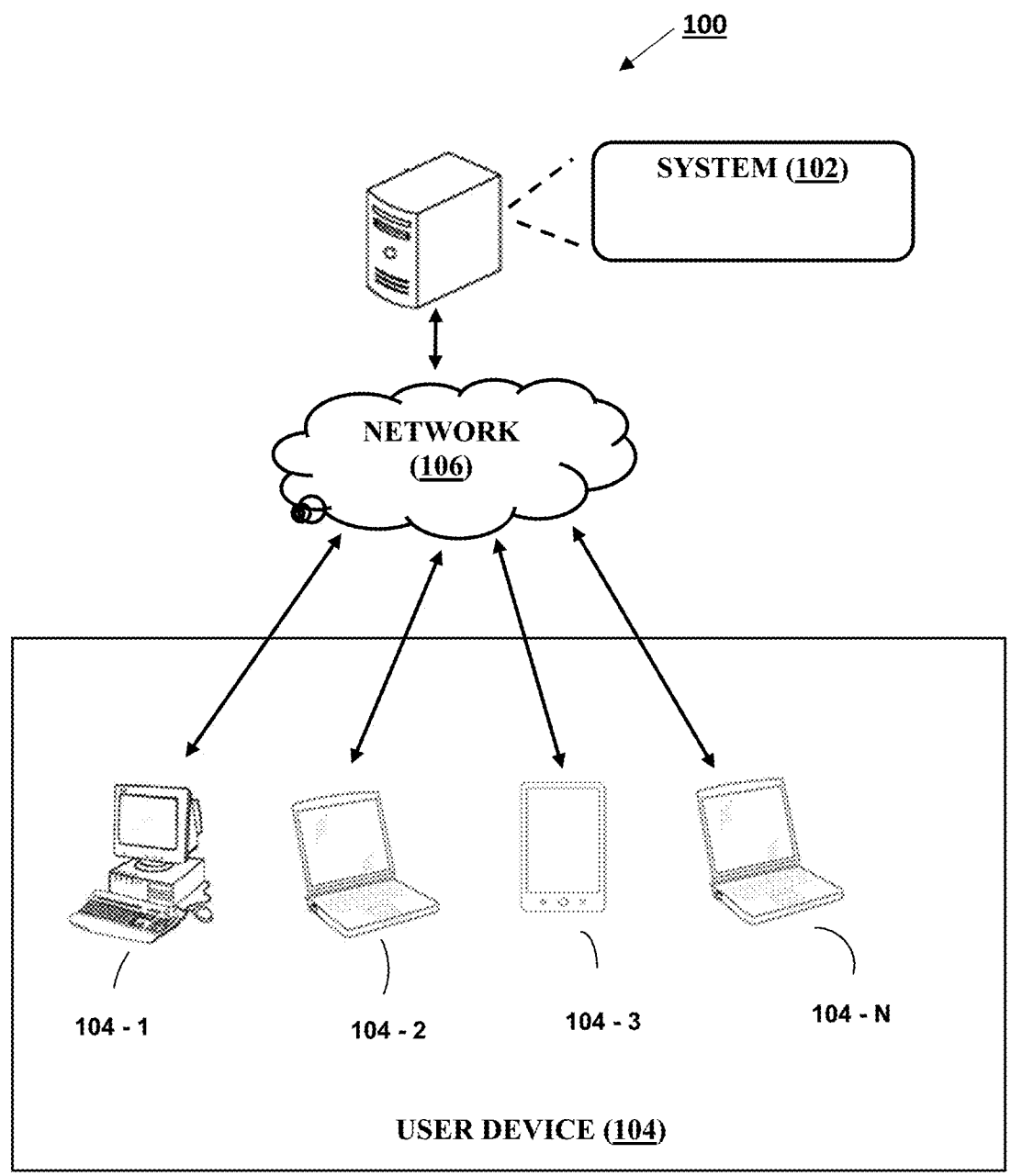
FIG. 1 illustrates a network implementation of a system 102 for Electro-Anatomical Mapping (EAM), in accordance with an embodiment of the invention.

Referring now to FIG. 1, a network implementation 100 of a system 102 for electro-anatomical mapping is disclosed. Although the present subject matter is explained considering that the system 102 is implemented on a server, it is to be understood that the system 102 may also be implemented in a variety of computing systems, such as a laptop computer, a desktop computer, a notebook, a workstation, a mainframe computer, a server, a network server, and the like. In one implementation, the system 102 may be implemented over a cloud network. Further, it will be understood that the system 102 may be accessed by multiple users through one or more user devices 104-1, 104-2 . . . 104-N, collectively referred to as user device 104 hereinafter, or applications residing on the user device 104. Examples of the user device 104 may include, but are not limited to, a portable computer, a personal digital assistant, a handheld device, and a workstation. The user device 104 may be communicatively coupled to the system 102 through a network 106.

In one implementation, the network 106 may be a wireless network, a wired network or a combination thereof. The network 106 may be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

Figure 2:
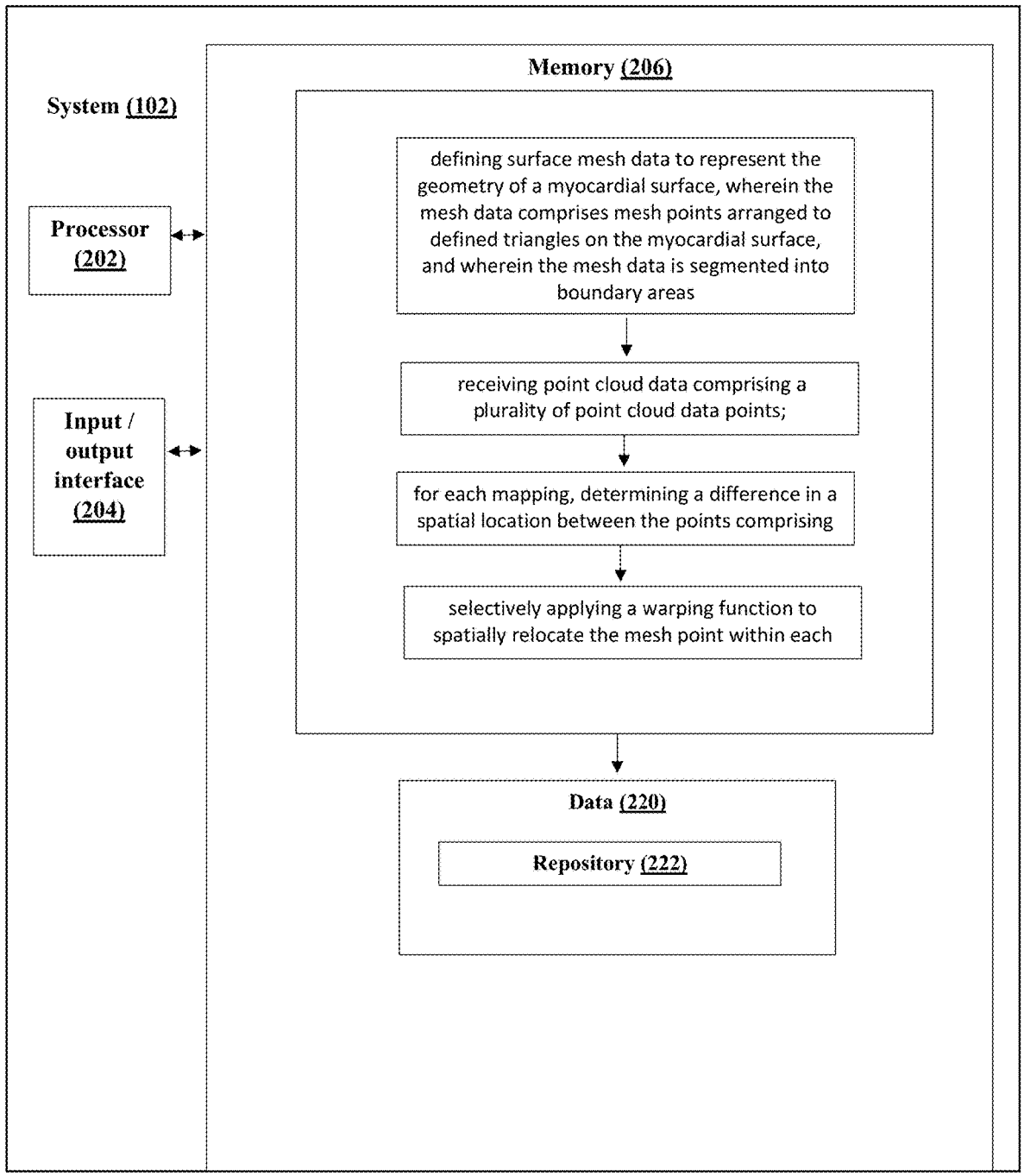
FIG. 2 illustrates component details of the system 102 as shown in FIG. 1 for the EAM, in accordance with an embodiment of the invention.

Referring now to FIG. 2, component details of the system 102 for electro-anatomical mapping is illustrated, in accordance with an embodiment of the present subject matter.

In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, at least one processor 202 may be configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with the user directly or through the user device 104. Further, the I/O interface 204 may enable the system 102 to communicate with other computing devices, such as web servers and external data servers (not shown). The I/O interface 204 may facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to each another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include one or more modules and data 210.

The modules may include routines, programs, objects, components, data structures, and the like, which perform particular tasks, functions or implement particular abstract data types. In one implementation, the module 206 may the configured with modules forceless instructions to perform the steps indicated, which will be described in greater detail below.

The data 210 may include data generated during execution of the steps, and may further include data required for the execution of said steps.

Figure 3:
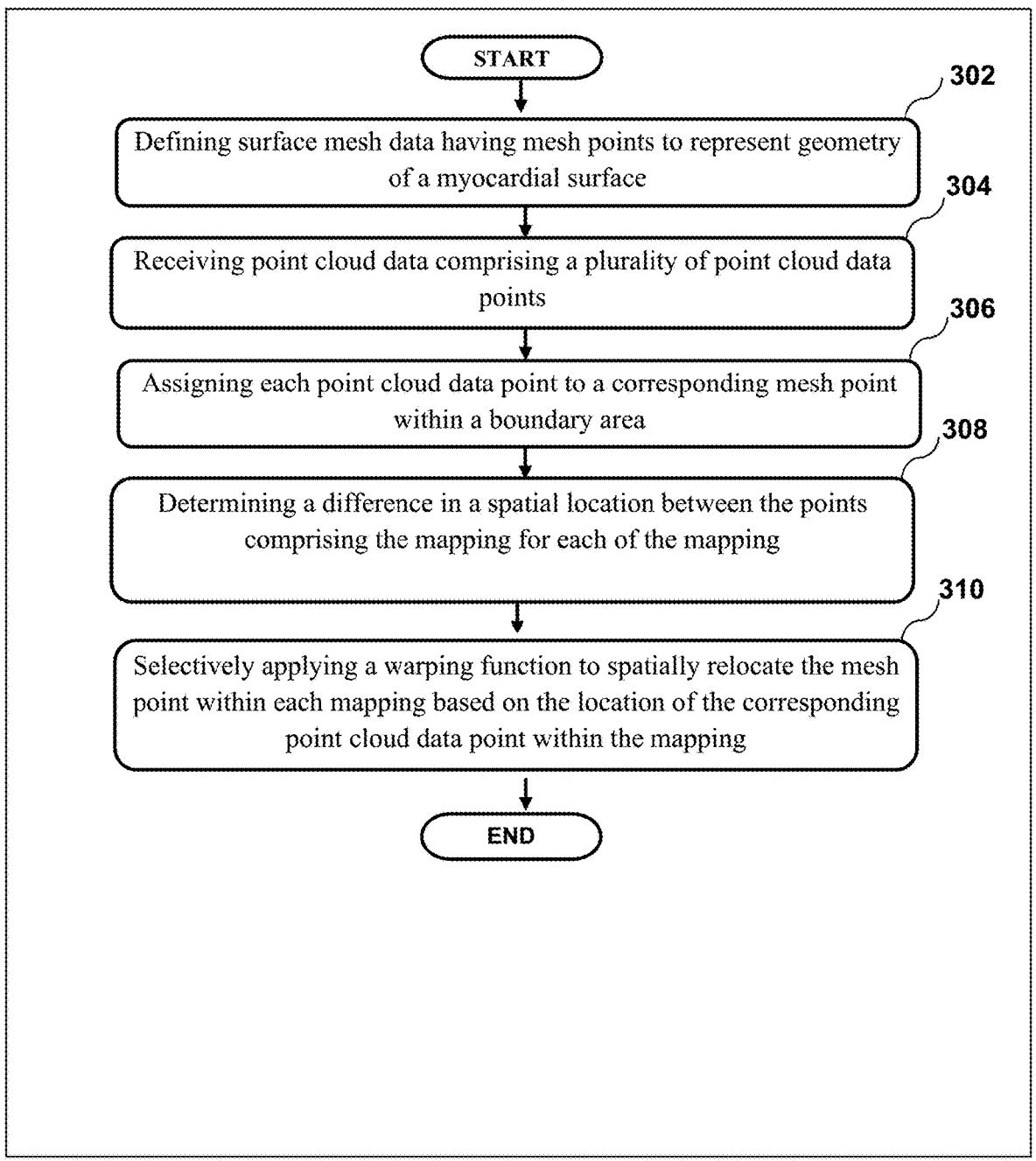
FIG. 3 illustrates for a method for the EAM, in accordance with an embodiment of the invention.

In an embodiment, referring to FIG. 3, a method 300 for electro-anatomical mapping executed by system 102 is shown. As will be seen, at step 302, surface mesh data to represent the geometry of a myocardial surface is defined. The surface mesh data comprises mesh points arranged to define triangles on the myocardial surface. In one embodiment, the surface mesh data may be segmented into boundary areas. For example At step 304, point cloud data is received.

At step 306, each point cloud data point is assigned to a corresponding mesh point within a boundary area. The point cloud data point and its corresponding mesh point defines a mapping.

At step 308, for each mapping a difference is determined in a spatial location between the points comprising the mapping.

At step 310, a warping function is selectively applied to spatially relocate the mesh point within each mapping based on the location of the corresponding point cloud data point within the mapping.

A result of the method 300 is a modified surface mesh that accurately reflects the geometry of a patient's heart. Advantageously, the modified mesh is generated by warping a minimal set of points in a precursor or template mesh thereby to produce the modified mesh.

In some embodiments, a smoothing function may be applied to the modified mesh in order to improve its resolution.

In another exemplary embodiment, the system 102 may be coupled to an electromagnetic tracking system (not shown) configured to track the position of a mapping catheter within the heart and is configured to receive incoming cloud point data comprising the plurality of point cloud data points (3D points) from said tracking system. The point cloud data points are defined in terms of XYZ coordinates (cartesian coordinates).

It is observed that the point cloud data may include a superimposition of a variety of ambient noise, instrumentation noise and physiological noises. The physiological noises are produced due to muscle contractions, respiration process and movements of body whereas, instrumentation noises are produced due to power cables, multichannel and electromagnetic interference of components.

The system 102 generates a high-resolution geometry of a patient's heart by performing the electro-anatomical mapping and renders visualizations of electro-anatomical mapping as detailed electro-anatomical maps on an output device (e.g. a display monitor) associated with interface 204.

Figure 4:
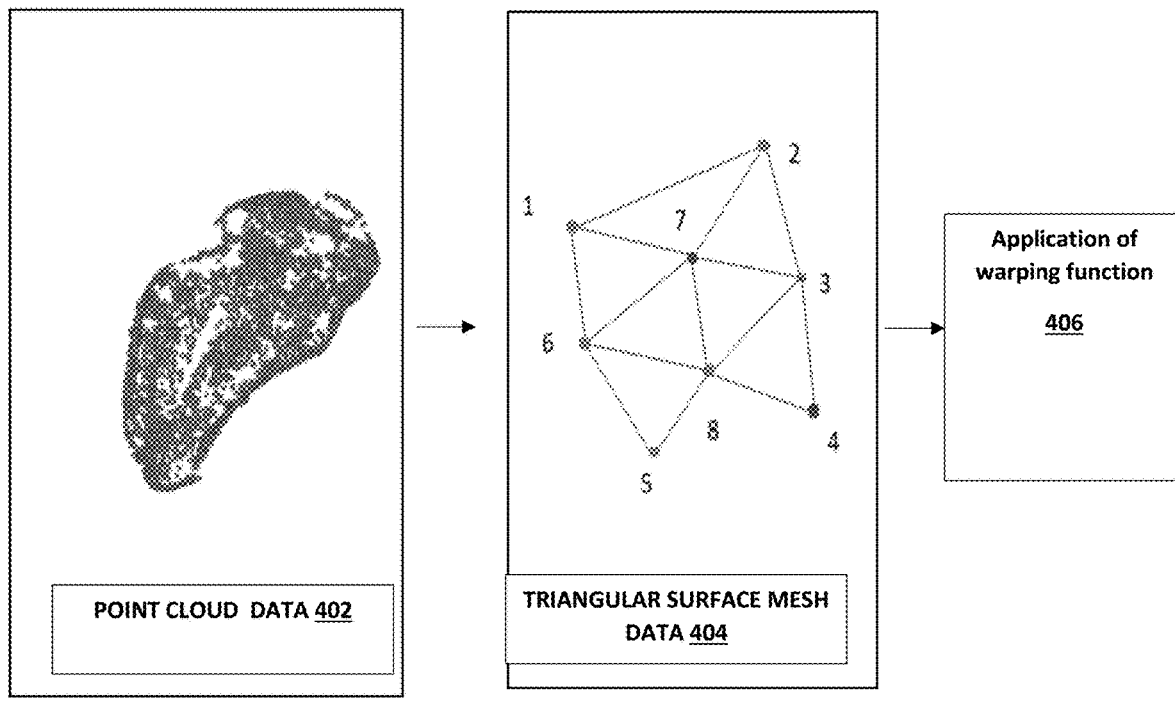
FIG. 4 illustrates warping of a surface mesh to produce a modified mesh, in accordance with an embodiment of the invention.

FIG. 4 illustrates how the point cloud data may be mapped to a surface mesh for a heart, in accordance with one embodiment of the invention. Referring to FIG. 4 incoming point cloud data 402 is mapped point-by-point a predefined surface mesh representing the service geometry of the heart. The mesh comprises a plurality of mesh points that are interconnected to define triangular regions that lie on the surface of the heart. Reference 404 shows a few of the mesh points. As part of the mapping process, each point from the point cloud data 404 is mapped to a corresponding point from the surface mesh data, based on the spatial location of the points. Thereafter, at block 406, a warping function is applied to warp selected points of the surface mesh.

In one embodiment, the surface mesh data comprises boundary areas each defining or corresponding to structures within the heart, for example, a left ventricle and a right ventricle.

The segmentation of the mesh data into boundary areas may be performed for controlling the mapping of incoming cloud point data to the mesh data.

Advantageously, warping of the surface mesh data may be performed selectively to spatially relocate the mesh point within each mapping based on the location of the corresponding point cloud data point within the mapping. The selectively application of the warping function is based on a threshold that defines a maximum value by which the mesh point is permitted to be spatially relocated.

After the selective application of the warping function, the processor is configured a smoothing function may be applied to smooth selective areas of the resultant mesh so as to avoid the artifact introduced by the warping process.

It will be appreciated by persons skilled in the art that the present invention is not limited to what has been particularly shown and described herein above. Rather, the scope of the present invention includes both combinations and Sub combinations of the various features described hereinabove, as well as variations and modifications there of that are not in the prior art, which would occur to persons skilled in the art upon reading the foregoing descriptions.

The invention claimed is:

1. A method for electro-anatomical mapping, the method comprising:
    defining surface mesh data to represent a geometry of a myocardial surface, wherein the mesh data comprises mesh points arranged to defined triangles on the myocardial surface, and wherein the mesh data is segmented into boundary areas;
    receiving point cloud data during a mapping process, said point cloud data comprising a plurality of point cloud data points, each comprising electrical recordings taken at discrete measurement sites where a catheter tip is in contact with the myocardial surface;
    assigning each point cloud data point to a corresponding mesh point within a boundary area, wherein the point cloud data point and its corresponding mesh point defines a mapping;
    for each mapping, determining a difference in a spatial location between the points comprising the mapping and
    selectively applying a warping function to spatially relocate the mesh point within each mapping based on the spatial location of the corresponding point cloud data point within the mapping.

2. The method of claim 1, wherein selectively applying the warping function is based on a threshold that defines a maximum value by which the mesh point is permitted to be spatially relocated.

3. The method of claim 1, further comprising applying a smoothing function to the mesh points within each boundary area after selectively applying the warping function.

4. The method of claim 1, wherein the surface mesh data represents a geometry of a hypothetical heart.

5. The method of claim 4, wherein the geometry of the hypothetical heart is selected to approximate geometry of actual hearts seen in clinical practice so that the spatial relocation of the mesh points through selective warping is minimal.

6. The method of claim 1, wherein each boundary area represents anatomical features of an actual heart.

7. A system for electro-anatomical mapping, the system comprising:
    a memory; and
    a processor coupled to the memory, wherein the processor is configured to execute instructions stored in the memory to:
        define surface mesh data to represent a geometry of a myocardial surface, wherein the mesh data comprises mesh points arranged to defined triangles on the myocardial surface, and wherein the mesh data is segmented into boundary areas;
        receive point cloud data during a mapping process, said point cloud data comprising a plurality of point cloud data points, each comprising electrical recordings taken at discrete measurement sites where a catheter tip is in contact with the myocardial surface;
        assign each point cloud data point to a corresponding mesh point within a boundary area, wherein the point cloud data point and its corresponding mesh point defines a mapping;
        for each mapping, determine a difference in a spatial location between the points comprising the mapping; and
        selectively apply a warping function to spatially relocate the mesh point within each mapping based on the spatial location of the corresponding point cloud data point within the mapping.

8. The system of claim 7, wherein the processor is configured to:
    selectively apply the warping function based on a threshold that defines a maximum value by which the mesh point is permitted to be spatially relocated.

9. The system of claim 7, wherein the processor is configured to:
    apply a smoothing function to the mesh points within each boundary area after selectively applying the warping function.

10. The system of claim 7, wherein the surface mesh data represents a geometry of a hypothetical heart.

11. The system of claim 10, wherein the geometry of the hypothetical heart is selected to approximate the geometry of actual hearts seen in clinical practice so that the spatial relocation of the mesh points through selective warping is minimal.

12. The system of claim 7, wherein each boundary area represents anatomical features of an actual heart.

* * * * *